US00PP11414P

United States Patent [19]

Van Gaalen

[11] Patent Number: Plant 11,414

[45] Date of Patent: Jun. 13, 2000

[54] CAMPANULA PLANT NAMED 'MYSTERY'

[76] Inventor: Rene Van Gaalen, Noordhoornseweg 37, 2635 GC Den Hoorn, Netherlands

[21] Appl. No.: 09/087,920

[22] Filed: Jun. 1, 1998

[51] Int. Cl.[7] ..... A01H 5/00

[52] U.S. Cl. ..... Plt./263

[58] Field of Search ..... Plt./263

[56] References Cited

PUBLICATIONS

GTITM UPOVROM Citation for 'Mystery' as per QZ PBR 971100; Nov. 13, 1997.

*Primary Examiner*—Howard J. Locker

*Assistant Examiner*—Kent L. Bell

*Attorney, Agent, or Firm*—C. A. Whealy

[57] ABSTRACT

A new and distinct cultivar of Campanula named 'Mystery', characterized by its unique pink star-shaped flowers; long flowering period; freely branching habit with lateral shoots potentially forming at every node; dark green leaves; uniform flower display; floriferous with numerous flowers per plant; and excellent postproduction longevity.

2 Drawing Sheets

BACKGROUND OF THE INVENTION

The present invention relates to a new and distinct cultivar of Campanula plant, hereinafter referred to by the cultivar name 'Mystery'

The new cultivar was discovered and selected by the inventor as a naturally-occurring branch mutation of an unidentified white-flowered cultivar of *Campanula medium L.* in a cultivated area in Den Hoorn, The Netherlands.

Asexual reproduction of the new cultivar by tissue culture in Roelofarendsveen, The Netherlands, has shown that the unique features of this new Campanula are stable and reproduce true to type in successive propagations.

SUMMARY OF THE INVENTION

The new cultivar has not been observed under all possible environmental conditions. The phenotype may vary somewhat with variations in environment such as temperature, daylength, light intensity, soil types, and water/fertility levels without, however, any variance in genotype. The following observations, measurements, values, and comparisons describe plants grown in Den Hoorn, The Netherlands, under production conditions which closely approximate those generally used in commercial horticulture.

The following traits have been repeatedly observed and are determined to be the unique characteristics of the new Campanula. These characteristics in combination distinguish 'Mystery' as a new and distinct Campanula:

1. Unique pink star-shaped flowers.
2. Long flowering period.
3. Freely branching habit with lateral shoots potentially forming at every node; plants do not require pinching.
4. Dark green leaves.
5. Uniform flower display.
6. Floriferous with numerous flowers per plant.
7. Excellent postproduction longevity; cut flowers last about 14 days after harvesting.

The new Campanula is distinct from other cultivars of *Campanula medium L.* known to the inventor in its unique narrow and separated petals giving the flower a star-shaped appearance. Additionally, plants of the new Campanula have been observed to flower longer than other *Campanula medium L.* cultivars.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of typical plants of 'Mystery' grown as cut flowers in ground beds.

The photograph on the second sheet comprises a close-up view of a flowering stem of a plant grown as a cut flower. Unopened flowers are also apparent in these photographs. Foliage and flower colors may appear different in the photographs than the actual colors due to light reflectance.

DETAILED BOTANICAL DESCRIPTION

The following description of the new cultivar is based on plants produced in Den Hoorn, The Netherlands, under glasshouse production conditions with average day and night temperatures of 20° C. Color references are made to The Royal Horticultural Society Colour Chart except where general terms of ordinary dictionary significance are used.

Botanical classification: *Campanula medium L.* cultivar 'Mystery.'

Parentage: Naturally-occurring branch mutation of an unidentified white-flowered cultivar of *Campanula medium L.*

Propagation:

*Type.*—By tissue culture and by cuttings.

*Root description.*—Fine and fibrous.

*Time to initiate roots.*—About 10 days at 21° C.

*Time to develop roots.*—About 15 days at 21° C.

Plant description:

*General appearance.*—Herbaceous perennial cut flower that may also be produced as a containerized plant. Rosette at base with upright flowering stem. Freely branching with one break potentially forming at every node.

*Crop time.*—About three months are required to produce a flowering plant.

*Lateral branch description.*—Diameter: About 2 mm. Internode length: About 3 cm. Texture: Pubescent, ridges. Color: 137B.

*Foliage description.*—Arrangement: At base, leaves arranged in a rosette; at apex, leaves alternate. Shape: Upper leaves: Linear with pointed apex and attenuate base. Lower leaves: Spatulate with rounded to dentate apex, base attenuate. Margin: Upper leaves: Entire. Lower leaves: Serrate. Length: Upper leaves: About 6.25 cm. Lower leaves: About 7 cm. Width: Upper leaves: About 1.5 cm. Lower leaves: About 2 cm. Texture: Upper leaves: Leathery; upper and lower surfaces, pubescent. Lower leaves: Leathery and rough; veins and margins, pubescent. Color: Upper leaves, upper surface: 147A. Upper leaves, lower surface: 147A. Lower leaves, upper surface: 147A. Lower leaves, lower surface: 147B. Petiole: Lower leaves not stalked. Length, upper leaves: About 4.75 cm. Diameter, upper leaves: About 2.5 mm at base. Color, upper leaves: 147C.

FLOWER DESCRIPTION:

*Natural flowering season.*—April/May in the Northern Hemisphere.

*Flower arrangement.*—Flowers arranged singly at lateral apices. Flowers face outward. Freely flowering.

*Fragrance.*—Faint.

*Flower appearance.*—Very large showy star-shaped single flowers. Typically five primary petals; occasionally secondary diminutive petals may be formed interior to the primary petals. Secondary petals inwardly curved, 7.5 mm by 4 mm in size. Flowers persistent.

*Flower diameter.*—About 14 cm.

*Flower depth (height).*—About 1 cm.

*Postproduction longevity.*—About 14 days as a cut flower.

*Petals.*—Appearance: Shiny. Texture: Smooth. Arrangement: Large single flowers. Shape: Narrow, linear with rounded, dentate or divided apex. Margin: Entire. Length: About 6.75 cm. Width: About 1 cm. Color, when opening: Greenish white. Color, fully opened: Primary petals, upper and lower surfaces: 62A to 63B. Secondary petals (if present): 62B to white.

*Sepal.*—Arrangement: Four to six sepals fused into a star-shaped calyx. Texture: Leathery. Shape: Linear with pointed apex. Margin: Entire. Color, upper and lower surfaces: 146B.

*Reproductive organs.*—Androecium: Stamen number: About five to seven. Anther shape: Linear/lanceolate. Anther size: About 1 mm. Amount of pollen: Moderate. Pollen color: 8A. Gynoecium: Stigma color: Yellow-green. Style length: About 2.5 cm. Style color: Yellow-green, white at base.

Disease resistance: Resistance to pathogens common to *Campanula medium* has not been observed.

Seed production: Seed production has not been observed.

It is claimed:

1. A new and distinct cultivar of Campanula named 'Mystery', as illustrated and described.

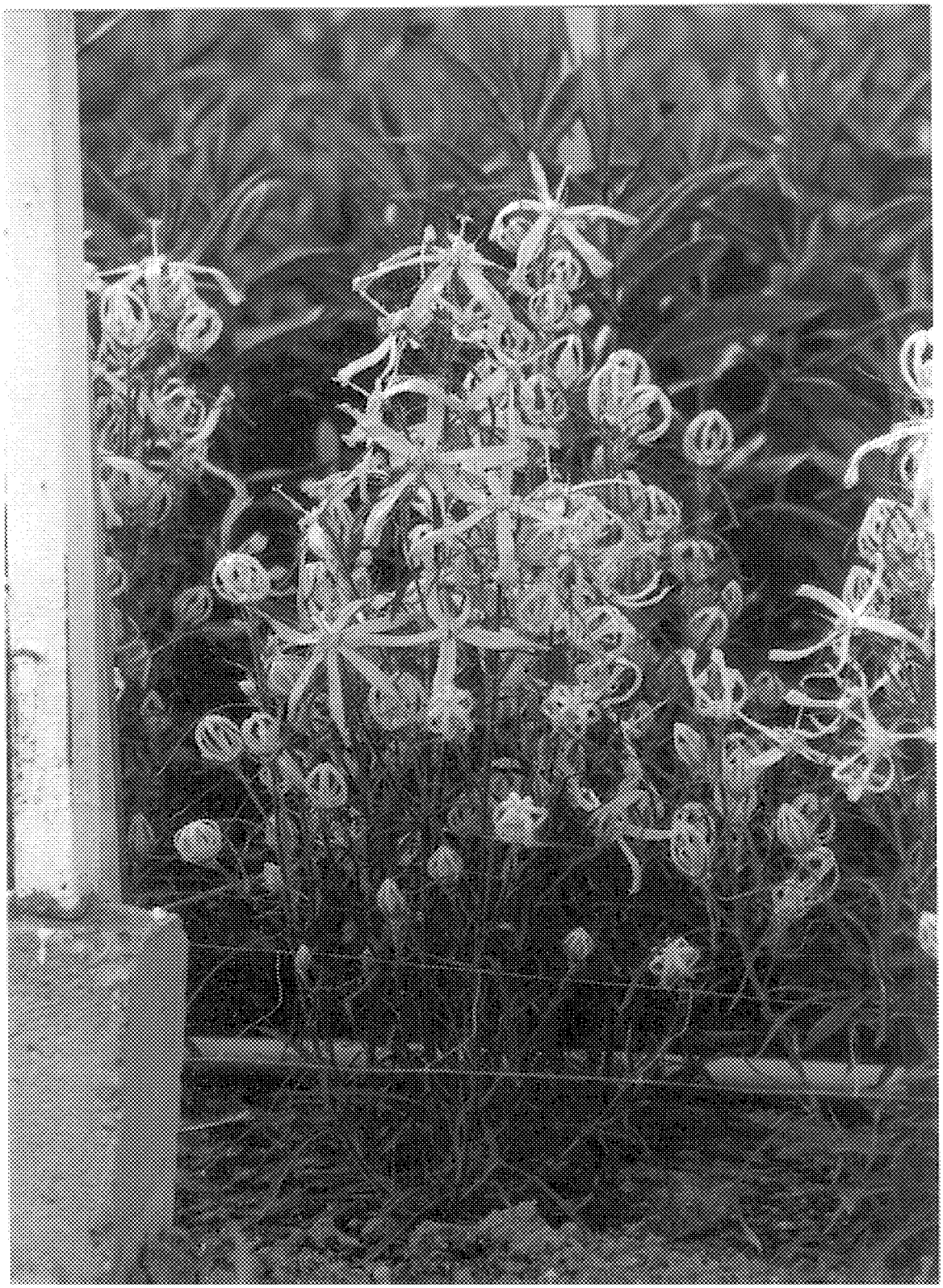

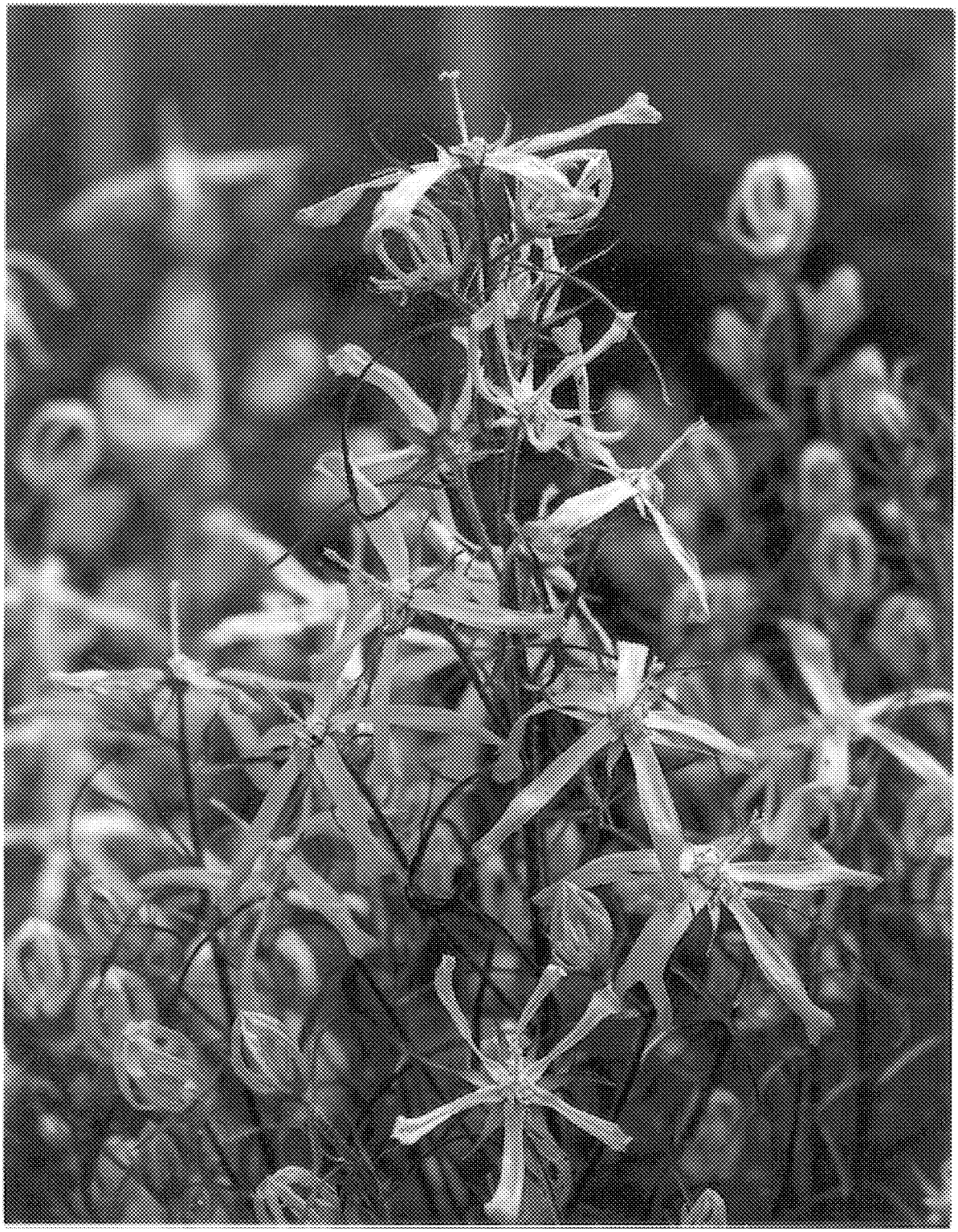

* * * * *